United States Patent [19]
Arai et al.

[11] Patent Number: 5,496,518
[45] Date of Patent: Mar. 5, 1996

[54] INCUBATOR

[75] Inventors: Kenji Arai; Yoshihiro Seto; Fumio Sugaya, all of Kanagawa, Japan

[73] Assignee: Fuji Photo Film Co., Ltd., Kanagawa, Japan

[21] Appl. No.: 355,178

[22] Filed: Dec. 8, 1994

[30] Foreign Application Priority Data

Dec. 9, 1993 [JP] Japan .................. 5-308979

[51] Int. Cl.$^6$ .................................................. G01N 37/00
[52] U.S. Cl. ........................ 422/64; 422/63; 422/104; 435/809; 435/303.1; 436/43; 436/46
[58] Field of Search .................. 422/63, 64, 65, 422/66, 67, 68.1, 104; 435/290, 316, 809; 436/43, 46, 164, 165, 805

[56] References Cited

U.S. PATENT DOCUMENTS

| | | | |
|---|---|---|---|
| 4,219,529 | 8/1980 | Tersteeg et al. | 422/65 |
| 4,298,571 | 11/1981 | DiFulvio et al. | 422/65 |
| 4,584,275 | 4/1986 | Okano et al. | 435/290 |
| 4,807,984 | 2/1989 | Kurimura et al. | 350/529 |
| 4,855,109 | 8/1989 | Muraishi et al. | 422/63 |
| 4,943,415 | 7/1990 | Przybylowicz et al. | 422/56 |
| 5,034,191 | 7/1991 | Porte | 422/64 |
| 5,075,079 | 12/1991 | Kerr et al. | 422/64 |
| 5,106,583 | 4/1992 | Raysberg et al. | 422/64 |
| 5,154,889 | 10/1992 | Muraishi | 422/65 |
| 5,207,987 | 5/1993 | Kureshy et al. | 422/67 |
| 5,219,526 | 6/1993 | Long | 422/64 |

Primary Examiner—James C. Housel
Assistant Examiner—Lone V. Le
Attorney, Agent, or Firm—Sughrue, Mion, Zinn, Macpeak & Seas

[57] ABSTRACT

A dry frameless chemical analysis film includes a support sheet and a reagent layer formed on the support sheet. An incubator for incubating the film spotted with a sample liquid includes an incubator base on which the frameless chemical analysis film is placed, an incubator cell member which is movable up and down between a lower position and an upper position and presses a part of the upper surface of the frameless chemical analysis film against the incubator base while tightly enclosing a space around the frameless chemical analysis film in the lower position, and a first heater which heats the part of the incubator base with which the frameless chemical analysis film is brought into contact to a first predetermined temperature and holds the same at the first predetermined temperature, and a second heater which heats the incubator cell member to a second predetermined temperature higher than the first predetermined temperature.

3 Claims, 7 Drawing Sheets

INCUBATOR

BACKGROUND OF THE INVENTION

1. Field of the Invention

This invention relates to an incubator for a biochemical analysis apparatus in which a sample liquid such as blood or urine is spotted on a reagent layer (spreading layer) of a dry frameless chemical analysis film and the concentration of a predetermined biochemical substance in the sample liquid is determined through a change in the optical density of the reagent layer due to a chemical reaction, a biochemical reaction, an immunoreaction or the like of the reagent in the reagent layer with the predetermined biochemical substance, the incubator being for incubating the frameless chemical analysis film spotted with the sample liquid at a constant temperature to promote the reaction.

2. Description of the Prior Art

There has been put into practice a chemical analysis slide having a "dry-to-touch" chemical analysis film with which the content of a specific chemical component contained in a sample liquid, the activity thereof or the content of a solid component can be quantitatively analyzed by only spotting a droplet of the sample liquid on the film. When quantitatively analyzing the chemical components or the like contained in a sample liquid using such a chemical analysis slide, a droplet of the sample liquid is spotted on the film (on the spreading layer when the film is provided with a spreading layer and directly on the reagent layer when the film is not provided with a spreading layer) and is held at a constant temperature for a predetermined time (incubation) in an incubator so that coloring reaction occurs, and the optical density of the color formed by the coloring reaction is optically measured. That is, measuring light containing a wavelength which is preselected according to the combination of the component to be analyzed and the reagent contained in the reagent layer of the film is projected onto the film and the optical density of the film is measured. Then the concentration or the activity of the component to be analyzed is determined on the basis of the optical density using a calibration curve which represents the relation between the concentration of the predetermined biochemical substance and the optical density.

The chemical analysis slide generally comprises a dry chemical analysis film chip and a frame of organic polymer which holds flat the chemical analysis film chip which is apt to curl or warp in a dry state. The chemical analysis film chip is generally composed of a support sheet of organic polymer or the like and at least one reagent layer (containing therein a reagent) formed on the support sheet. Preferably a spreading layer is formed on the reagent layer.

However the chemical analysis slide is disadvantageous in that each of the parts of the incubator for incubating the chemical analysis slides must be larger in size by the amount corresponding to the size of the frame, which obstructs reduction in size of the biochemical analysis apparatus and at the same time results in reduction of the number of the chemical analysis films which can be accommodated in an incubator of a given size. When the number of the chemical analysis films which can be accommodated in an incubator is small, the overall throughput capacity of the biochemical analysis apparatus cannot be increased.

In view of the observation, we have proposed to use a chemical analysis film chip without the frame (will be referred to as a "frameless chemical analysis film", hereinbelow). However since the frameless chemical analysis film is apt to curl in a dry state as described above and the state of curl changes when the sample liquid is spotted thereon, the frameless chemical analysis film should be held flat in the incubator. Further the frameless chemical analysis film should be held tightly enclosed in the incubator.

In the incubator, the frameless chemical analysis film spotted with the sample liquid is heated to a predetermined temperature and held at the temperature. For instance, in U.S. Pat. Nos. 4,219,529 and 4,298,571, there is disclosed an incubator for the chemical analysis slides in which a chamber is provided to cover a plurality of cells each for accommodating one chemical analysis slide and the atmosphere in the chamber is heated to and held at a predetermined temperature.

In the chamber, each chemical analysis slide must be held in place in order to keep constant the distance from the light measuring optical system, to facilitate inserting and taking out the slide into and from the incubator, and to transmit heat to the slide. In the United States patents identified above, each slide is held in place by a spring-like pressing member. Since the spring-like pressing member is not ready to transmit heat due to its shape, the temperature in the chamber is controlled and the pressing member (including a cover which is brought into contact with the slide by the pressing member) are heated by way of air. In order to keep constant the temperature in the chamber, the chamber is kept closed.

Since the pressing member is heated through air in such an incubator having a temperature-controlled chamber, the temperature of the pressing member is lowered when a cold slide is inserted into the chamber and it takes a long time for the pressing member to recover the predetermined incubating temperature. (Generally the slides are stored at a low temperature to prevent deterioration of the measuring performance and accordingly the temperature of the slide before insertion into the chamber is low.) In order to suppress such a problem, it is necessary to pre-heat the slide before insertion into the chamber so that the fluctuation in temperature of the pressing member is suppressed. Further upon starting up the biochemical analysis apparatus, it takes a long starting-up time to heat the atmosphere in the incubator to the predetermined incubating temperature due to the air heating structure of the chamber.

Further in the air heating structure of the chamber, the chamber must be tightly enclosed in order to keep constant the temperature in the chamber, which requires a shutter for opening and closing the slide port and complicates the structure of the incubator. Further since the cells for accommodating the slides are enclosed in the chamber, interfering gas which can be generated during coloring reaction in one of the cells and can affect the coloring reaction in another cell is confined in the chamber, which can result in deterioration in accuracy of measurement. Further, the members for sealing the chamber, the mechanism of shutter and the like adds to the manufacturing cost of the incubator. Thus it is preferred that the slide be heated tightly enclosed in each cell so that the coloring reaction in each cell cannot be affected by evaporation of the sample liquid or interfering gases confined in the chamber.

There has also been known a technique in which a plurality of cells each for accommodating a slide are formed in a base plate of metal and a pressing member is provided to tightly enclose, from above, the slide accommodated in each cell, the base plate being heated by heater and the pressing member being heated by way of an upper member which supports the pressing member and is heated by a heater wound therearound. In this technique, the chamber is not necessary.

When dry frameless chemical analysis films are incubated in such an incubator in which no chamber is formed and the frameless chemical analysis films are directly heated, the shutter for opening and closing the slide port can be eliminated, preheating of the slide becomes unnecessary, the starting-up time can be shortened, and the problem of influence of interfering gases can be avoided. However since the part of the upper side of the frameless chemical analysis film on which the sample liquid is applied cannot be directly touched, the part of the frameless chemical analysis film cannot be sufficiently heated to the incubating temperature.

That is, when a frameless chemical analysis film in a curled state is flattened by a flat pressing member, the lower side of the pressing member is brought into contact with the sample liquid on the film and the sample liquid adheres to the pressing member and can contaminate the sample liquid on the frameless chemical analysis film to be incubated next when the pressing member flattens the next film.

Thus, in the case of the frameless chemical analysis film, it is preferred that the film be heated only by conduction of heat from the lower side thereof without contact heating of the upper side of the film. In this case, the frameless chemical analysis film can be held flat, for instance, by pressing down a part of the margin of the film which is free of the sample liquid. However since the incubator cell must tightly enclose the film to prevent evaporation of the sample liquid and must be able to surely hold the film irrespective of fluctuation in the state of curl and/or thickness of the film, the incubator cell becomes complicated in structure. Further in order to reduce the amount of interfering gas and/or the sample liquid adhering to the incubator cell, it is preferred that the incubator cell be molded from a limited plastic material.

When the incubator cell is formed from plastic material, a problem of moisture condensation is involved due to low heat conductivity of the plastic material. That is, since the frameless chemical analysis film in the incubator cell is heated by heat from the lower side and the heat of the film is hard to be transmitted to the incubator cell due to a small contact area between the film and the incubator cell, the film can be surely heated to a predetermined temperature. On the other hand, since the temperature of the inner surface of the incubator cell is kept low and the enclosed space in the incubator cell is held at 100% humidity, moisture is condensed on the inner surface of the incubator cell, which adversely affects the measurement and involves problems due to absorption of interfering gases.

SUMMARY OF THE INVENTION

In view of the foregoing observations description, the primary object of the present invention is to provide an improved incubator in which the frameless chemical analysis film can be incubated in an enclosed and flattened state while being heated by direct heating from the lower side and in which the problem of moisture condensation can be avoided.

The incubator in accordance with the present invention is for incubating a dry frameless chemical analysis film which comprises a support sheet and a reagent layer formed on the support sheet and is spotted with a sample liquid and the incubator comprises an incubator base on which the frameless chemical analysis film is placed, an incubator cell member which is movable up and down between a lower position and an upper position and presses a part of the upper surface of the frameless chemical analysis film against the incubator base while tightly enclosing a space around the frameless chemical analysis film in the lower position, a first heating means which heats the part of the incubator base with which the frameless chemical analysis film is brought into contact to a first predetermined temperature and holds the same at the first predetermined temperature, and a second heating means which heats the incubator cell member to a second predetermined temperature higher than the first predetermined temperature.

It is preferred that the second predetermined temperature be higher than the first predetermined temperature by 6° C. at highest. Further it is preferred that the second heating means heats the incubator cell member by way of a metal member disposed on the outer surface of the incubator cell member.

In the incubator of the present invention, the frameless chemical analysis film spotted with the sample liquid is inserted into the incubator and is pressed flat against the incubator base and tightly enclosed by the incubator cell member. In this state, the frameless chemical analysis film is heated to and held at the incubating temperature (the first predetermined temperature) by heat transmitted through the incubator base which is heated by the first heating means while the incubator cell member is heated to the second predetermined temperature higher than the incubating temperature by the second heating means, whereby the temperature of the inner surface of the incubator cell member is kept higher than the incubating temperature and moisture condensation on the inner surface of the incubator cell member is prevented.

Thus the frameless chemical analysis film can be incubated without involving deterioration of accuracy of measurement and at the same time, the chamber can be eliminated and the advantages of direct heating can obtained. Further since the frameless chemical analysis film without frame is used, the incubator can be compact in size and the cost of biochemical analysis can be lowered.

DESCRIPTION OF THE PREFERRED EMBODIMENT

Figure 1:
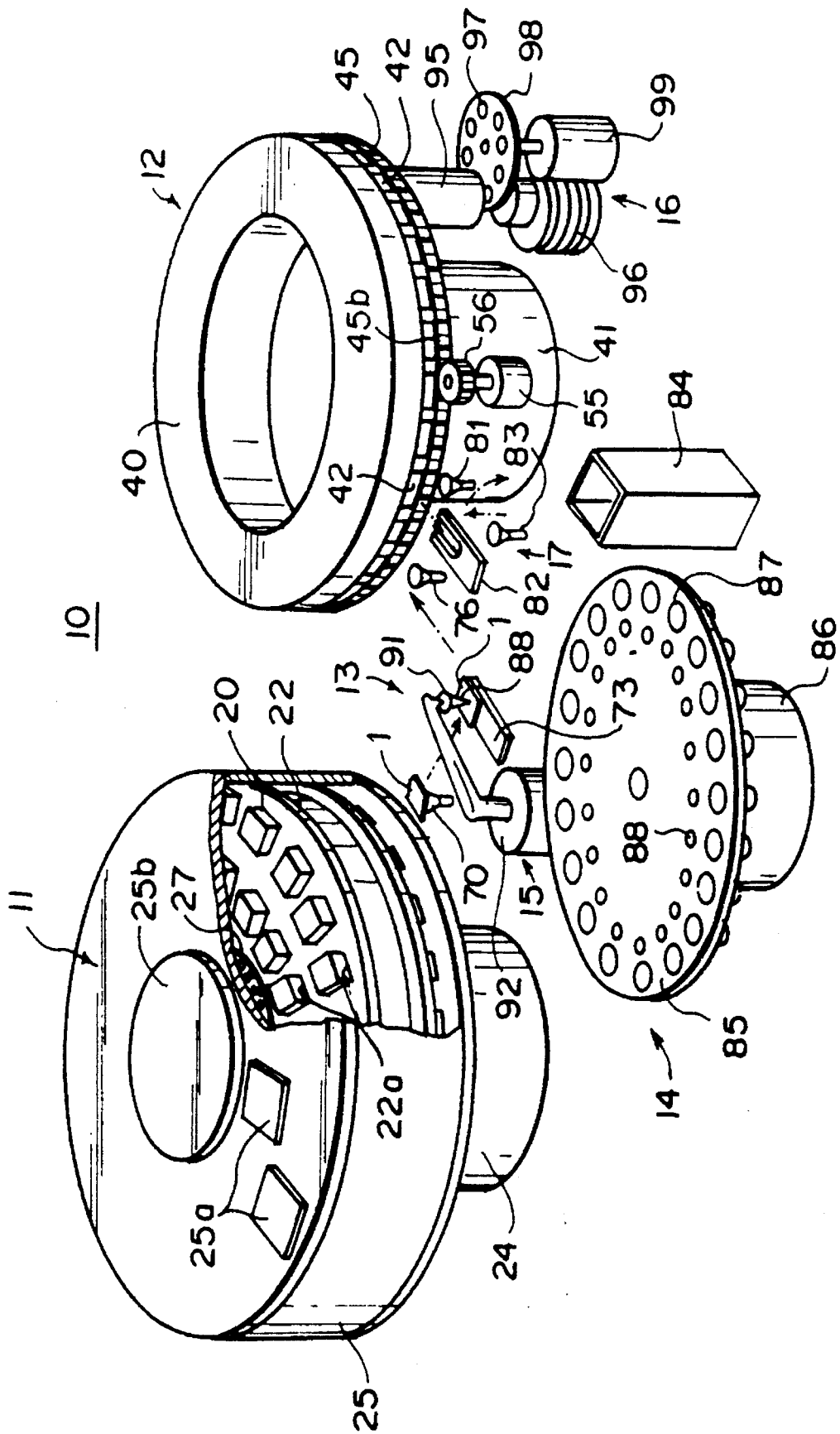
FIG. 1 is a perspective view showing a biochemical analysis apparatus provided with an incubator in accordance with an embodiment of the present invention.

In FIG. 1, a biochemical analysis apparatus 10 provided with an incubator in accordance with an embodiment of the present invention comprises a film supplier 11 in which a plurality of rectangular dry frameless chemical analysis films 1 are stored, an incubator 12 which is disposed beside the film supplier 11 and incubates the frameless chemical analysis films 1 transferred from the film supplier 11 for a predetermined time at a constant temperature, a film transfer means 13 which transfers the frameless chemical analysis films 1 from the film supplier 11 to the incubator 12, a sample liquid supplier 14 in which a plurality of sample liquids such as serum, urine or the like are stored, a spotting mechanism 15 which spots one of the sample liquids in the sample liquid supplier 14 on the frameless chemical analysis film 1 on the way to the incubator 12, and a light measuring system 16 disposed below the incubator 12.

Figure 2:
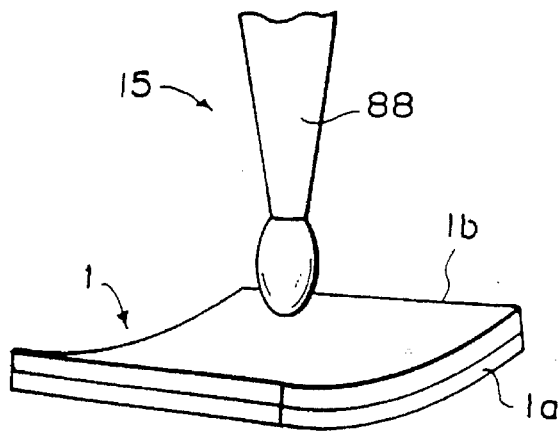
FIG. 2 is a perspective view showing spotting of the sample liquid on the frameless chemical analysis film.

As shown in FIG. 2, the frameless chemical analysis film 1 comprises a light-transmissive support sheet or support sheet 1a formed of plastic film such as polyethylene terephthalate, polystyrene or the like and a reagent layer 1b (including a spreading layer) formed on the support sheet 1a. If necessary, a wear-resistant protective layer of fibrous material such as fabric may be formed on the reagent layer 1b. Such a protective layer may double as the spreading layer.

More particularly, the frameless chemical analysis film 1 is formed by coating or bonding a reagent layer portion of a reagent layer 1b on a support sheet 1a and laminating a spreading layer portion on the reagent layer portion. It should be noted that the film is not provided with any frame. The reagent layer portion comprises at least one layer composed of a porous layer or a hydrophilic polymer binder such as gelatin containing therein a detecting reagent component which selectively reacts with an analyte and a reagent component (chemical analysis reagent or immunoassay reagent) which is necessary for coloring reaction. The spreading layer portion is formed of woven or knitted fabric (or cloth) of synthetic fiber resistant to rubbing such as polyester, or of blend of natural fiber and synthetic fiber, unwoven fabric or paper and functions as a protective layer. Further the spreading layer causes sample liquid applied thereto to uniformly spread over the reagent layer.

Though the dry frameless chemical analysis film 1 is substantially flat under a normal humidity condition, the film 1 is apt to curl toward the reagent layer 1b in a dry state before spotting of the sample liquid since the film 1 is stored under a dry condition (e.g., at a humidity not higher than 20%), and the degree of curl varies depending on the dryness and the kind of the reagent layer 1b. The reagent layer 1b makes coloring reaction (coloring substance forming reaction) when it is mixed with a particular component in the sample liquid spotted by a nozzle tip 88 of the spotting mechanism 15 and is incubated at a constant temperature for a predetermined time. A plurality of kinds of frameless chemical analysis films 1 having different reagent layers 1b are prepared according to the items or analytes of analysis, e.g., the chemical components or solid components to be analyzed in the sample liquids.

The frameless chemical analysis films 1 are stored in cartridges 20 (FIG. 3) for the respective items of analysis. In the cartridge 20, a plurality of the frameless chemical analysis films 1 are stacked with the support sheets 1a facing downward. As shown in FIG. 1, the film supplier 11 is provided with a plurality of cartridge holding portions 22a which are arranged in inner and outer circles on a disk-like support 22 and a plurality of cartridges 20 loaded with the frameless chemical analysis films 1 are held in the respective cartridge holding portions 22a. The support 22 is supported for rotation on a base portion 24 and is rotated by a supplier motor (not shown) disposed in the base portion 24 so that a predetermined cartridge holding portion 22a is brought to a film takeout position where the film transfer means 13 takes out a frameless chemical analysis film 1 from the cartridge 20.

The support 22 is provided with a cover 25 which tightly encloses the inner space of the film supplier 11. The cover 25 is provided with a pair of openings 25a provided with lids and the cartridges 20 can be taken out and inserted into the cartridge holding portion 22a through the openings 25a. An dehumidifying agent holding portion 27 is formed in the support 22 at the center thereof and dehumidifying agent is loaded in the dehumidifying agent holding portion 27 through an opening 25b formed in the cover 25. The opening 25b is provided with a lid. Thus the inner space of the film supplier 11 is kept dry.

A film takeout port (not shown) is provided in the lower surface of the cover 25 in the film takeout position and a shutter is provided to open and close the film takeout port. The shutter is opened when the frameless chemical analysis film 1 is taken out from the cartridge 20 and a suction pad 70 of the film transfer means 13 is inserted into the film supplier 11 through the shutter and takes out the lowermost film 1 in the cartridge 20.

The incubator 12 comprises a disk-like body portion 40 which is rotatably supported on a base 41 disposed below the body portion 40 at the center thereof. A plurality of cells 42 are provided in the body portion 40 at predetermined intervals in the circumferential direction thereof. The frameless chemical analysis films 1 are incubated in the cells 42.

As shown in more detail in FIGS. 4 to 8, the body portion 40 comprises an incubator base (lower disk) 45 having a flat upper surface. An annular cell cover 46 is provided on the incubator base 45 along the peripheral edge of the upper surface of the incubator base 45. The lower edge of the outer peripheral edge of the cell cover 46 is spaced from the upper surface of the incubator base 45 to form a side opening 42a which opens in the side surface of the incubator 12 and through the frameless chemical analysis film 1 is inserted into the incubator 12.

A cylindrical rotational shaft 45a is provided on the incubator base 45 to extend downward from the center of the incubator base 45. The rotational shaft 45a is supported on the base 41 by way of a bearing 50 to be rotatable relative to the base 41 which is fixed. Teeth 45b are formed on the outer peripheral surface of the incubator base 45 and in mesh with a drive gear 56 which is mounted on an output shaft of a drive motor 55, whereby the incubator base 45 is driven by the drive motor 55. An under cover 53 is provided on the lower surface 40 of the body portion 40.

A plurality of light measuring windows 59 are formed in the incubator base 45 to be opposed to the respective cells 42, and an incubator cell member 64 for tightly enclosing the space in which the frameless chemical analysis film 1 is accommodated is provided above each of the light measuring windows 59 to be slidable relative to the cell cover 46. A film pressing member 61 which presses flat the frameless chemical analysis film 1 and fixes the film 1 in a predetermined position is provided in the incubator cell member 64. The outer surface of the cell cover 46 is coated with heat insulation material 51. A measuring system 16 has a light measuring head 95 which is disposed below the light measuring window 59 of the body portion 40 in a light measuring position.

Figure 6:
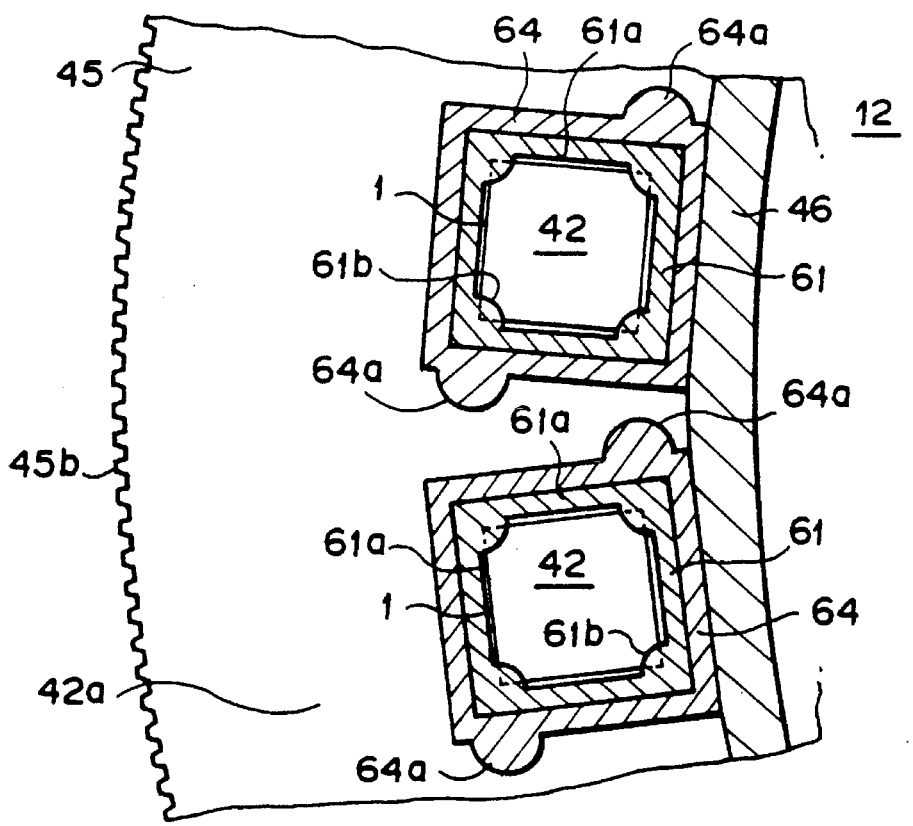
FIG. 6 is a cross-sectional view taken along line 6—6 in FIG. 5.
Figure 7:
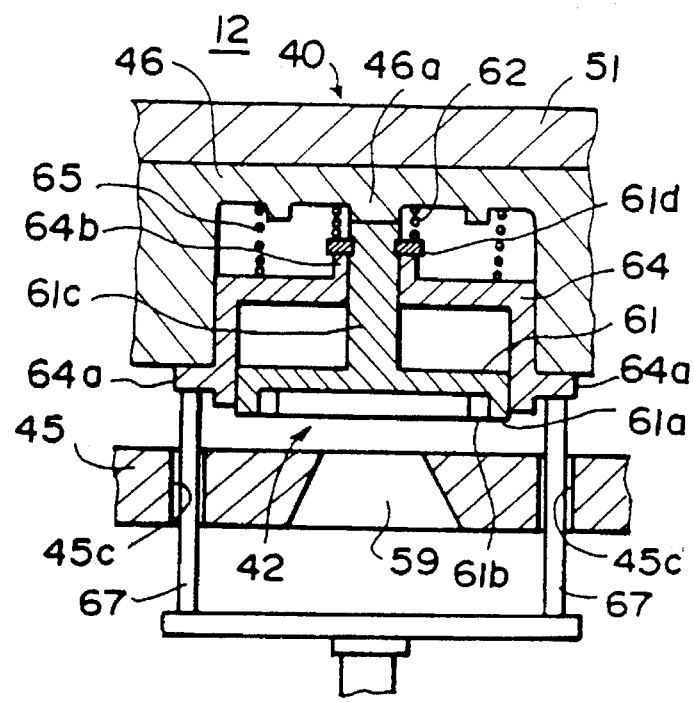
FIG. 7 is a fragmentary cross-sectional view of the incubator as seen in the radial direction of the incubator.
Figure 8:
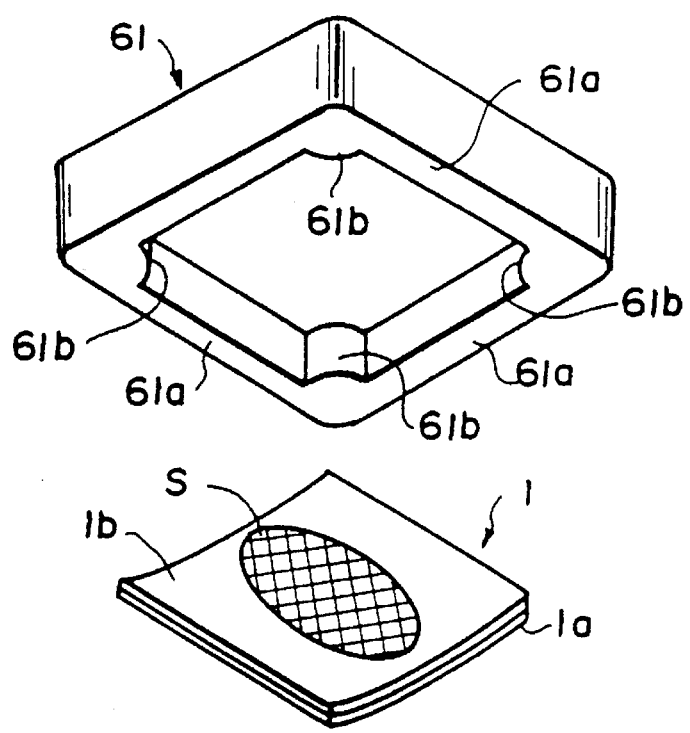
FIG. 8 is a perspective view showing the film pressing member in relation to the frameless chemical analysis film spotted with the sample liquid.

The film pressing member 61 presses the film 1 at corner portions thereof outside the spread S (FIG. 8) of the sample liquid. That is, the film pressing member 61 has a rectangular frame portion 61*a* on the lower surface thereof as shown in FIGS. 6 and 8. The inner dimensions of the frame portion 61*a* is larger than the outer dimensions of the frameless chemical analysis film 1 and a protrusion 61*b* is provided at each corner of the frame portion 61*a* to project inward. When the film pressing member 61 is moved downward against the film 1, only the protrusions 61*b* are brought into contact with the film 1. The film pressing member 61 has a shank portion 61*c* extending upward from the top of the pressing member 61 and a spring 62 for urging downward the film pressing member 61 is compressed between a spring retainer 61*d* provided on the shank portion 61*c* and the cell cover 46.

When the spread S of the sample liquid extends in the transverse direction of the frameless chemical analysis film 1 as shown in FIG. 8, the protrusions 61*b* of the film pressing member 61 may be shaped to press the upper and lower edges of the film 1.

The incubator cell member 64 has a box-like body portion open downward and is positioned to surround the film pressing member 61. The shank portion 61*c* of the film pressing member 61 extends through the upper surface of the body portion at the center thereof. A guide portion 64*b* is formed on the upper surface of the body portion to guide the film pressing member 61 to move up and down in parallel to the incubator cell member 64. The incubator cell member 64 is fitted in the cell cover 46 to be slidable up and down and is urged downward under the force of a spring 65 provided between the top wall of the incubator cell member 64 and the cell cover 46. The lower surface of the incubator cell member 64 is pressed against the upper surface of the incubator base 45 to tightly enclose therein the frameless chemical analysis film 1. The film pressing member 61 is received in the incubator cell member 64 to be slidable up and down relative to the incubator cell member 64. When the incubator cell member 64 is moved upward, the film pressing member 61 is moved upward together with the incubator cell member 64 by way of an engagement between the retainer 61*d* and the guide portion 64*b*.

A first heater 48 is disposed on the inner side of the upper surface of the incubator base 45 and a heater cover 54 is provided on the first heater 48. The incubator base 45 is formed of material having high heat conductivity such as aluminum. The first heater 48 is controlled to heat the portion of the incubator base 45 which is in contact with the frameless chemical analysis films 1 in the cells 42 to a predetermined incubating temperature (e.g., 37° C.) on the basis of the output of a temperature sensor 49 (FIG. 5) disposed in the incubator base 45 near the cell 42, whereby the frameless chemical analysis film 1 which is pressed flat against the upper surface of the incubator base 45 is directly heated to the incubating temperature and is held at the temperature.

A second heater 57 is provided on the outer peripheral surface of the cell cover 46. As clearly shown in FIG. 5, the second heater 57 is fixed to a metal (e.g., aluminum) band 58 wound around the cell cover 46. The second heater 57 is controlled to heat the cells 42 to a temperature (e.g., 39° C. to 43° C.) higher than the incubating temperature by 6° C. at most on the basis of the output of a temperature sensor 66 disposed in the cell cover 46. By so setting the temperature of the cells 42, the temperature of the incubator cell member 64 and the film pressing member 61 cannot be lowered below the incubating temperature (e.g., 37° C.) even if the environmental temperature lowers, for instance, to 15° C.

The incubator cell member 64 and the film pressing member 61 are formed of black polyethylene in order to suppress contamination due to adsorption of gases and influence of internal reflection of small amount of light transmitted through the film 1 on the light measurement. The cell cover 64 is formed of plastic material.

Since the film pressing member 61 can be moved up and down relative to the incubator cell member 64, frameless chemical analysis films 1 having different thicknesses can be surely pressed flat by the film pressing member 61 while tight enclosure of the frameless chemical analysis film 1 is ensured. The fluctuation in the thicknesses of the films 1 is 1 mm at most, and the inner space of the incubator cell member 64 is actually narrow though it is exaggerated in the drawings.

A pair of engaging portions 64*a* (FIGS. 6 and 7) are formed on diagonally opposed corners of the lower portion of the incubator cell member 64 and a pair of through holes 45*c* are formed in the incubator base 45 to opposed to the engaging portions 64*a*. A pair of rods 67 are provided in a film insertion position and in a film takeout position. The rods 67 are moved upward through the holes 45*c* to abut against the engaging portions 64*a* of the incubator cell member 64 and lifts upward the incubator cell member 64 together with the film pressing member 61 when the frameless chemical analysis film 1 is to be inserted into the cell 42 or taken out therefrom.

Figure 4:
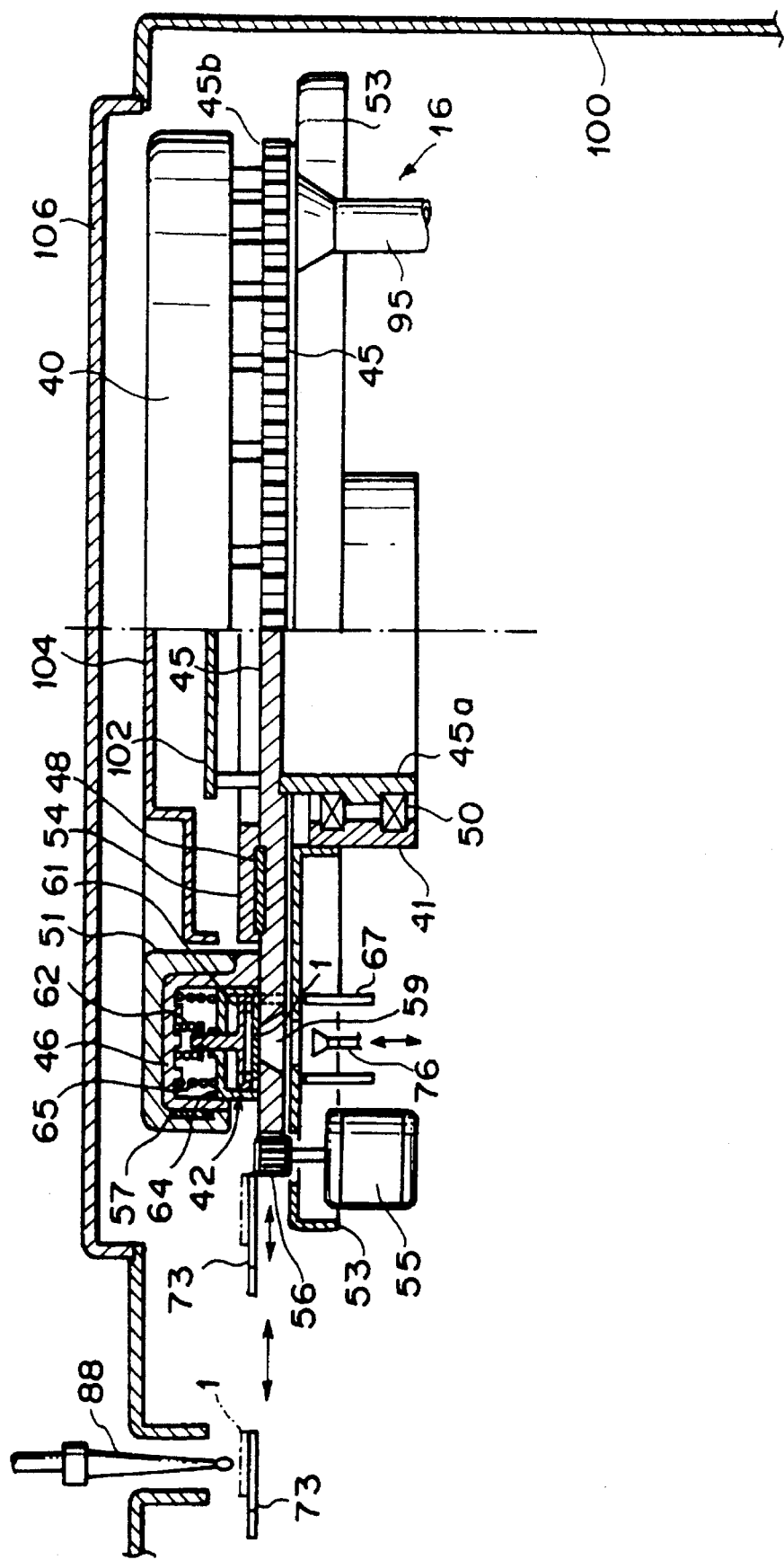
FIG. 4 is a front view partly in cross-section of the incubator.

As shown in FIG. 4, a cover 104 covers the incubator base 45 inside the cell cover 46, and a printed circuit board 102 for controlling the temperatures in the incubator 12 and the like are disposed inside the cover 104. The overall biochemical analysis apparatus 10 is enclosed in an apparatus cover 100, and a 106 is provided in the apparatus cover 100 above the incubator 12.

The film transfer means 13 for transferring the frameless chemical analysis film 1 from the film supplier 11 to the incubator 12 comprises said suction pad 70 which takes out the film 1 from the cartridge 20, a horseshoe-like film transfer member 73 which receives the film 1 held on the suction pad 70 from below the film 1 with the reagent layer 1*b* facing upward and inserts the film 1 into the incubator 12 through the opening 42*a* which opens sideways, and a suction member 76 which moves in and out the incubator 12 from below and receives the film 1 held by the film transfer member 73 inside the incubator 12.

Figure 3:
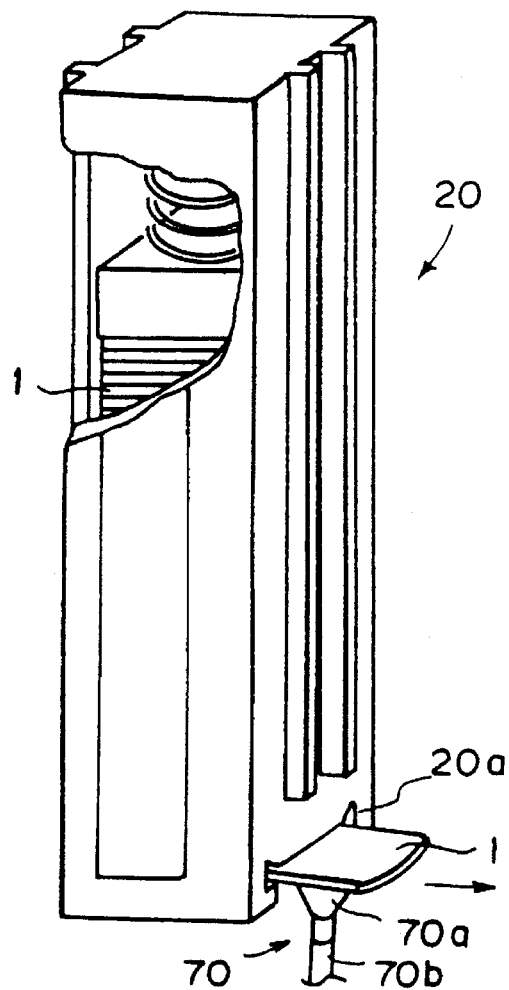
FIG. 3 is a perspective view showing the operation of taking out the frameless chemical analysis film from the cartridge.

As shown in FIG. 3, the suction pad 70 comprises a suction cup 70*a* which is directed upward and attracts the lower side of the support sheet 1*a* of the frameless chemical analysis film 1. The suction cup 70*a* is supported on a base portion 70*b* which is moved back and forth and is connected to a suction pump (not shown) through a vacuum tube.

The suction pad 70 is moved upward into the cartridge 20 through an opening in the bottom of the cartridge 20 and attracts the lowermost frameless chemical analysis film 1 on the support sheet side thereof. Then the suction pad 70 is slightly moved downward to curl the lowermost film 1 and then horizontally moved to take out the film 1 from the cartridge through an opening 20*a* in the side wall of the cartridge with the film 1 held in the curled state. Thereafter the suction pad 70 is moved downward outside the film supplier 11 through the film takeout port in the film supplier 11 and is moved toward a spotting position where the sample liquid is spotted on the film 1.

Figure 9:
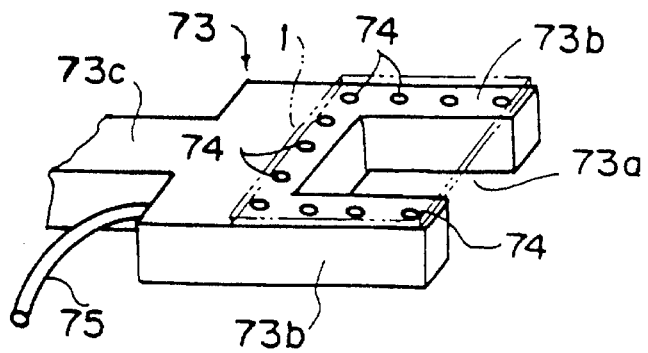
FIG. 9 is a fragmentary perspective view of the film transfer member.

As shown in FIG. 9, the film transfer member 73 is like a horseshoe in shape and has a flat upper surface. That is, the film transfer member 73 is bifurcated in the front end portion to form a pair of arm portions 73b extending on opposite sides of a cutaway portion 73a, and a plurality of suction holes 74 are formed to surround the cutaway portion 73a and to open in the upper surface of the film transfer member 73. The suction holes 74 are connected to a suction pump (not shown) through a vacuum tube 75. The base portion 73c of the film transfer member 73 is connected to a drive mechanism (not shown) to be inserted into the cell 42 in the incubator 12 through the opening 42a.

Figure 10A:
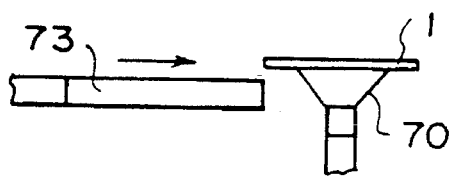
FIGS. 10A to 10C are schematic views for illustrating procedure for transferring the film from the suction pad to the film transfer member.
Figure 10B:
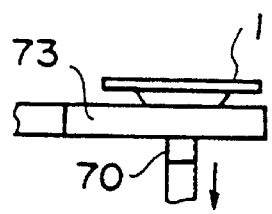
Figure 10C:
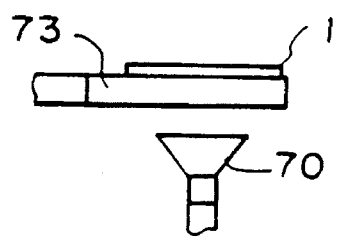

When the film transfer member 73 receives the film 1 from the suction pad 70, the film transfer member 73 is moved toward the suction pad 70 holding the film 1 as shown in FIG. 10A and is stopped in a position where the suction pad 70 is in the cutaway portion 73a of the film transfer member 73 with the film 1 positioned above the cutaway portion 73a as shown in FIG. 10B. Then the suction pad 70 is moved downward below the film transfer member 73 leaving the film 1 on the film transfer member 73 as shown in FIG. 10C. The film 1 left on the film transfer member 73 is held thereon under the suction force provided through the suction holes 74. Then a predetermined amount of the sample liquid is spotted on the center of the reagent layer 1b of the frameless chemical analysis film 1 held by the film transfer member 73.

Figure 5:
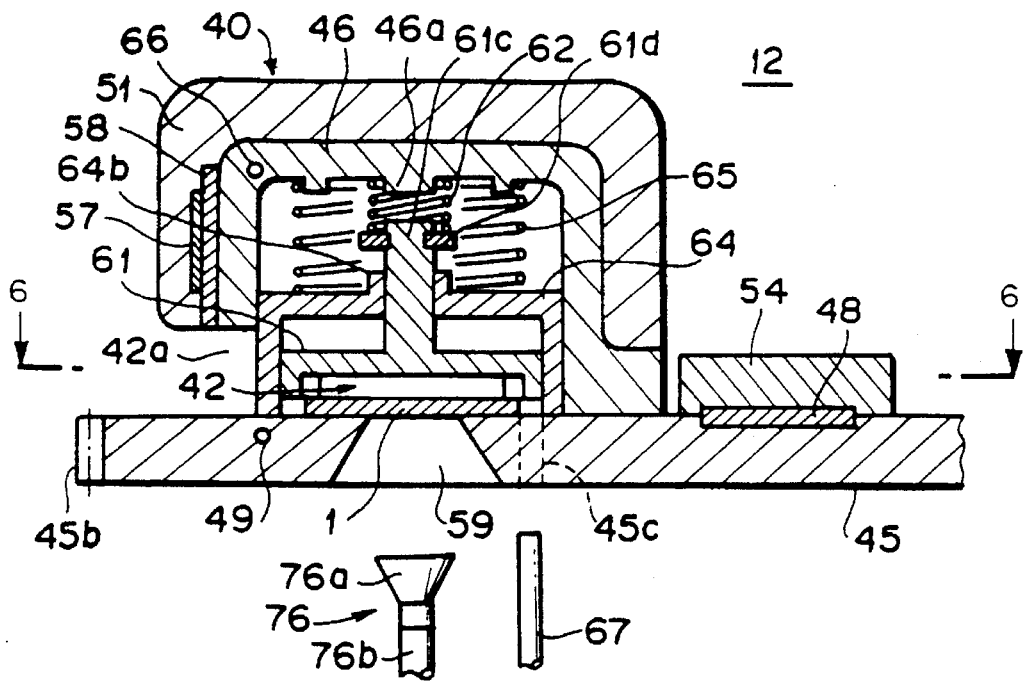
FIG. 5 is an enlarged fragmentary cross-sectional view showing the cell of the incubator.

As shown in FIG. 5, the suction member 76 is positioned below the cell 42 in the incubator 12 and comprises a suction cup 76a supported on a base portion 76b to be moved up and down by a drive mechanism not shown) into and away from the cell 42 through the light measuring window 59. The suction cup 76a is connected to a suction pump (not shown) through a vacuum hose.

A film removing means 17 (FIG. 1) is disposed in the film removing position of the incubator 12. The film removing means 17 comprises a removing suction pad 81 which attracts the film 1 in the cell 42 which has finished with measurement and lifts it, a horseshoe-like film removing member 82 which receives the film 1 from the removing suction pad 81 and transfers it outside the incubator 12 and a discarding suction pad 83 which receives the film 1 from the film removing member 82 and discards it into a discarding box 84.

The sample liquid supplier 14 comprises a turn table 85 which is rotated by a drive mechanism 86. The turn table 85 holds a plurality of sample tubes 87 filled with sample liquids which are arranged along the circumferential edge of the turn table 85 and is rotated to bring the sample tubes 87 to a sample liquid supplying position one by one. A plurality of nozzle tips 88 which are mounted on a spotting nozzle 91 to be described later are held on the turn table 85 inside the sample tubes 87.

The spotting means 15 for spotting the sample liquid on the frameless chemical analysis film 1 to be transferred to the incubator 12 comprises a spotting nozzle 91 which sucks and discharges the sample liquid, and a pipette-like nozzle tip 88 is demountably mounted on the nozzle 91. The nozzle 91 is moved up and down and rotated by a drive mechanism 92. That is, the nozzle 91 sucks the sample liquid from the sample liquid supplier 14, is moved to the film 1 held by the film transfer member 73, and then spots the sample liquid on the film 1. The nozzle tip 88 is changed every time the sample liquid is changed.

The film 1 spotted with the sample liquid is transferred to the incubator 12 and incubated there. After incubation for a predetermined time, the optical density of the reagent layer 1b is measured by the light measuring system 16 (FIG. 1) disposed below the incubator 12. The light measuring system 16 comprises said light measuring head 95 for measuring the optical density of the color formed by the coloring reaction between the reagent layer 1b and the sample liquid. The light measuring head 95 projects measuring light containing light of a predetermined wavelength onto the reagent layer 1b through the support sheet 1a and detects reflected light with a photodetector. Light from a light source (lamp) 96 enters the light measuring head 95 through an interference filter 97 and is caused to impinge upon the reagent layer 1b by the head 95. A plurality of kinds of the filters 97 are mounted on a rotary disk 98 which is driven by an electric motor 99 and one of the filters 97 is selected according to the item of measurement.

The reflected light from the reagent layer 1b carries thereon optical information (more particularly the amount of light) on the amount of coloring substances formed by the coloring reaction between the reagent layer 1b and the sample liquid. The reflected light is received by the photodetector and the optical information carried by the reflected light is converted to an electric signal by the photodetector. The electric signal is input into a determination section through an amplifier. The determination section determines the optical density of the coloring substance formed by the coloring reaction between the reagent layer 1b and the sample liquid on the basis of the level of the electric signal and determines the concentration of a predetermined chemical component in the sample liquid.

The measurement by the biochemical analysis apparatus 10 is effected in the following manner. That is, a frameless chemical analysis film 1 is taken out by the suction pad 70 of the film transfer means 13 from a cartridge 20 storing therein frameless chemical analysis films 1 corresponding to the item of measurement. The film 1 held by the suction pad 70 is transferred to the film transfer member 73 with the reagent layer 1b facing upward and a sample liquid is spotted on the reagent layer 1b.

That is, a nozzle tip 88 is mounted on the spotting nozzle 91 of the spotting means 15 and the spotting nozzle 91 is moved above a desired sample tube 87 in the sample liquid supplier 14. Then the nozzle 91 is moved downward to bring the nozzle tip 88 into the sample liquid and the nozzle 91 sucks a predetermined amount of the sample liquid into the nozzle tip 88. Thereafter the nozzle 91 is moved above the center of the film 1 on the film transfer member 73 and moved downward toward the film 1, where a predetermined amount of sample liquid is spotted on the reagent layer 1b from the nozzle tip 88. The sample liquid spreads over the reagent layer 1b and mixes with the reagent therein.

Figure 11A:
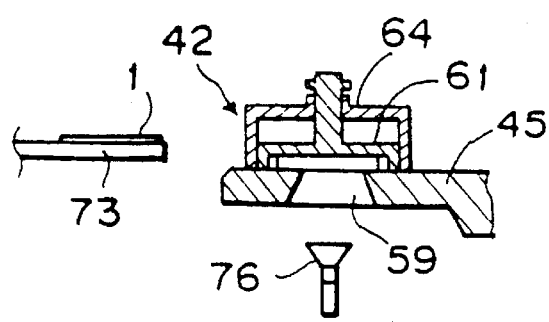
FIGS. 11A to 11G are schematic views for illustrating procedure for inserting the film into the incubator.
Figure 11E:
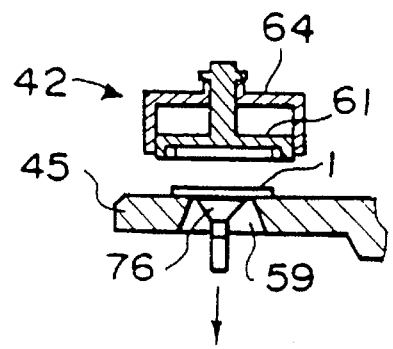
Figure 11B:
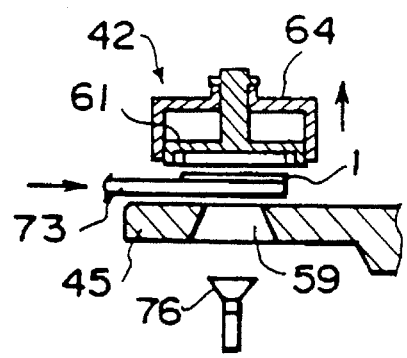
Figure 11F:
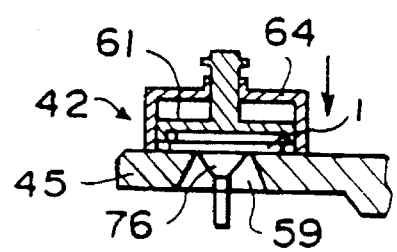
Figure 11C:
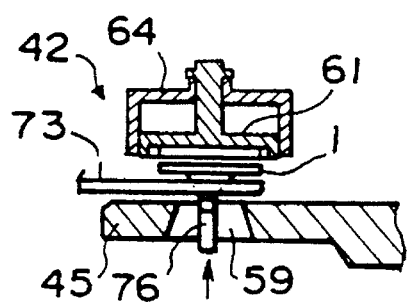
Figure 11G:
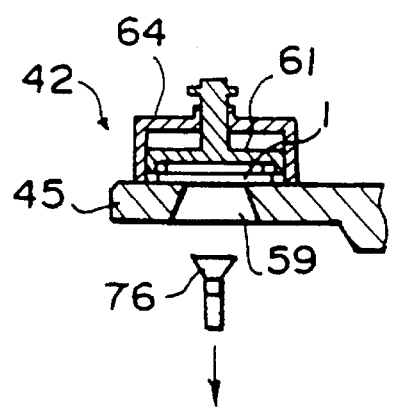
Figure 11D:
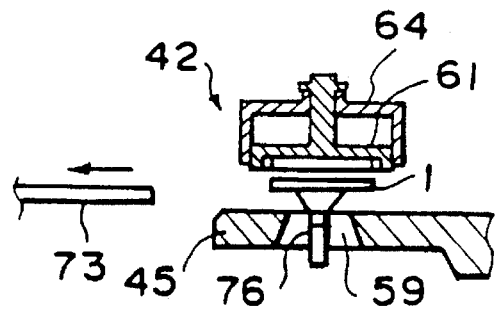

The film 1 spotted with the sample liquid is inserted into one of the cells 42 of the incubator 12 through the opening 42a by the film transfer member 73. When the film 1 is inserted into the cell 42, the incubator 12 is first rotated to bring a vacant cell 42 to the film insertion position as shown in FIG. 11A. Then the incubator cell member 64 is lifted together with the film pressing member 61 by the rods 67 and the film transfer member 73 is inserted into the cell 42 through the opening 42a as shown in FIG. 11B. Then the suction member 76 is moved upward and lifts the film 1 away from the film transfer member 73 as shown in FIG. 11C. When the suction member 76 lifts the film 1, it holds the film 1 under a suction force. After the film transfer member 73 is retracted away from the cell 42 as shown in FIG. 11D, the suction member 76 is moved downward so that the lower side of the film 1 abuts against the upper surface of the incubator base 45 of the incubator 12 as shown in FIG. 11E. Then the rods 67 are moved downward to permit the incubator cell member 64 and the film pressing member 61 to move downward as shown in FIG. 11F. In this state, the film 1 is tightly enclosed in the incubator cell member 64 with the four corners thereof held down by the protrusions 61b of the film pressing member 61. Then the suction member 76 is moved downward as shown in FIG. 11G.

Thus the film 1 is fixed in a predetermined position in the cell 42 and tightly enclosed by the incubator cell member 64. The light measuring window 59 is closed by the film 1 itself.

In the incubator 12, the frameless chemical analysis film 1 is pressed flat against the upper surface of the incubator base 45 by the film pressing member 61 and is heated to the incubating temperature by heat transmitted through the incubator base 45 while the frameless chemical analysis film 1 is tightly enclosed in the incubator cell member 64. Coloring reaction (coloring substance forming reaction) is caused when the film 1 with the sample liquid is heated to the incubating temperature in the cell 42 in the incubator 12, and the optical density of the coloring matter is measured by the light measuring head 95 after a predetermined time or at predetermined intervals.

Since the incubator cell member 64 and the film pressing member 61 are held at a temperature higher than the incubating temperature by the second heater 57, moisture condensation cannot occur on the inner surface of the incubator cell member 64 or on the surface of the film pressing member 61. Further since the second heater 57 is wound around the outer peripheral surface of the cell cover 46, the temperature of the incubator cell member 64 and the film pressing member 61 can be held at a predetermined temperature less affected by fluctuation in the temperature of the environment. Even if the temperature of the film pressing member 61 is somewhat higher than the incubating temperature, the frameless chemical analysis film 1 cannot be heated higher than the incubating temperature by the heat of the film pressing member 61 since the film pressing member 61 is in contact with the frameless chemical analysis film 1 in a small area.

Since the spring 62 for urging the film pressing member 61 is disposed outside the incubator cell member 64, the inner space of the incubator cell member 64 can be narrow. When the inner space of the incubator cell member 64 is narrow, evaporation of the sample liquid can be suppressed and the concentration of reaction gas which can be generated depending on the analyte can be held constant, whereby the reaction can be stabilized, and at the same time, the area of the inner surface of the incubator cell member 64 becomes small, whereby the amount of gas adsorbed by the wall of the incubator cell member 64 is reduced.

The incubator cell member 64 is arranged to be fit in the cell cover 46 and accordingly can be easily removed from the incubator 12 for cleaning or replacement. Further since the cell cover 46 can be easily removed from the incubator 12 and the upper surface of the incubator base 45 is flat, the upper surface of the incubator base 45 can be easily cleaned. Since the film pressing member 61 can slide up and down, frameless chemical analysis films 1 having different thicknesses can be surely fixed by the film pressing member 61.

Further since the engaging portions 64a of the incubator cell member 64 are formed on diagonally opposed corners of the lower portion of the incubator cell member 64, the space between the cell covers 64 can be smaller which results in miniaturization of the system, and at the same time the incubator cell member 64 can be lifted in a balanced position.

The incubator cell member 64 and the film pressing member 61 may be variously modified. For example, the spring for urging the film pressing member may be disposed inside the incubator cell member 64. In this case, only the spring for urging the incubator cell member 64 is disposed above the incubator cell member 64. Further the film pressing member may be formed integrally with the incubator cell member. For example, the film pressing member may be formed of an elastic material integrally with the incubator cell member on the inner side of the bottom of the incubator cell member so that the film pressing member is pressed against the corners of the film and is resiliently deformed under the force of the spring for urging downward the incubator cell member and the film is held flat under the resiliency of the film pressing member. Further a sealing member of a flexible material may be formed integrally with a film pressing member like that shown in FIG. 6 to extend downward from the film pressing member and to surround the film pressing member in a skirt-like fashion. When the film pressing member is pressed against the upper surface of the incubator base under the force of a spring, the sealing member is pressed against the upper surface of the incubator base to tightly enclose the film.

As described above, in accordance with the present invention, since the incubator base of metal is heated by the first heater and the frameless chemical analysis films are pressed against the incubator base to be directly heated by the incubator base, the films can be quickly heated and the preheating time can be shortened as compared with a system in which the films are heated on a disk positioned in a temperature-regurated chamber. Further the incubator in accordance with the present invention is advantageous over the latter system in that the chamber is not necessary, the thermal efficiency is high and a shutter for inserting the films into the chamber can be eliminated, whereby the incubator can be simple in structure. Further since the incubator cell member which is brought into contact with a part of the frameless chemical analysis film to fix the film is heated to a temperature higher than the incubating temperature, moisture condensation can be prevented and measurement can be effected under an optical condition.

What is claimed is:

1. An incubator for incubating a dry frameless chemical analysis film which comprises a support sheet and a reagent layer formed on the support sheet and is spotted on an upper surface with a sample liquid, the incubator comprising:

an incubator base on which the frameless chemical analysis film is placed, an incubator cell member which is movable up and down between a lower position and an upper position and presses a peripheral portion of the upper surface of the frameless chemical analysis film at a location outside of the sample liquid against the incubator base while also enclosing a space around the frameless chemical analysis film in the lower position, a first heating means which heats the incubator based at least at a location in which the frameless chemical analysis film is brought into contact with the incubator base when the incubator cell member is in the lower position, to a first predetermined temperature and holds the incubator base and in turn the frameless chemical analysis film at the first predetermined temperature, and a second heating means which heats the incubator cell member to a second predetermined temperature higher than the first predetermined temperature.

2. An incubator as defined in claim 1 in which said second predetermined temperature is higher than the first predetermined temperature by 6° C. at highest.

3. An incubator as defined in claim 1 in which the incubator cell member includes an outer surface, and wherein said second heating means heats the incubator cell member by way of a metal member disposed on the outer surface of the incubator cell member.

* * * * *